(12) United States Patent
Whiteley et al.

(10) Patent No.: US 8,933,008 B2
(45) Date of Patent: Jan. 13, 2015

(54) DISINFECTANT SOLUTION COMPRISING SYNERGISTIC, NON-EQUILIBRIUM ALDEHYDE BIOCIDES

(75) Inventors: Gregory Stuart Whiteley, Queenscliff (AU); Reginald Keith Whiteley, North Manly (AU); Graeme David Probert, Louth Park (AU); Trevor Owen Glasbey, Lemon Tree Passage (AU)

(73) Assignee: Whiteley Corporation Pty. Ltd. (AU)

( * ) Notice: Subject to any disclaimer, the term of this patent is extended or adjusted under 35 U.S.C. 154(b) by 85 days.

(21) Appl. No.: 13/643,722

(22) PCT Filed: Apr. 27, 2011

(86) PCT No.: PCT/AU2011/000472
§ 371 (c)(1),
(2), (4) Date: Dec. 19, 2012

(87) PCT Pub. No.: WO2011/134005
PCT Pub. Date: Nov. 3, 2011

(65) Prior Publication Data
US 2013/0203845 A1    Aug. 8, 2013

(30) Foreign Application Priority Data
Apr. 27, 2010    (AU) ................................ 2010901760

(51) Int. Cl.
*C11D 3/48* (2006.01)
*A01N 43/28* (2006.01)
*A01N 35/04* (2006.01)

(52) U.S. Cl.
CPC ................ *A01N 43/28* (2013.01); *A01N 35/04* (2013.01)

USPC .......................................................... 510/161

(58) Field of Classification Search
USPC .......................... 510/161, 382, 383, 461, 505
See application file for complete search history.

(56) References Cited

U.S. PATENT DOCUMENTS

| 4,748,279 | A | * | 5/1988 | Whiteley | 568/494 |
| 5,158,778 | A | * | 10/1992 | Donovan et al. | 424/488 |
| 6,071,972 | A | * | 6/2000 | Block | 514/698 |
| 2001/0009682 | A1 | | 7/2001 | Whiteley | |
| 2005/0171216 | A1 | * | 8/2005 | Zhu et al. | 514/699 |
| 2011/0104223 | A1 | * | 5/2011 | Li | 424/405 |

FOREIGN PATENT DOCUMENTS

| AU | 16302/83 B2 | 5/1987 |
| AU | WO2008116271 A1 | 10/2008 |
| CA | 2682515 | * 10/2008 |

* cited by examiner

*Primary Examiner* — Charles Boyer
(74) *Attorney, Agent, or Firm* — Andrew S. Langsam; Pryor Cashman, LLP

(57) ABSTRACT

A disinfectant solution comprising: an aldehyde; a polyol; one or more acetal derivatives formed by reaction of said aldehyde with said polyol; one or more surfactants selected from the general classes anionic, cationic, or non-ionic; one or more pH buffering agents selected from the group consisting of monosodium phosphate, disodium phosphate, trisodium phosphate, sodium tetraborate, sodium bicarbonate, sodium citrate, phosphoric acid, boric acid and citric acid. The invention also relates to a process of producing the disinfectant solution, and a method of disinfecting and/or sterilizing heat sensitive medical devices comprising treating the medical devices with the disinfectant solution of the invention.

23 Claims, 4 Drawing Sheets

DISINFECTANT SOLUTION COMPRISING SYNERGISTIC, NON-EQUILIBRIUM ALDEHYDE BIOCIDES

The present application is a U.S. national phase application under 35 USC §371 which claims priority on prior filed International Application PCT/AU2011/000472, filed Apr. 27, 2011. All description, drawings and teachings set forth therein are expressly incorporated by reference herein and claim to priority upon the teachings expressly made herein.

Ortho phthaldehyde (OPA) became a significant chemical high level disinfectant following the release of U.S. Pat. No. 4,971,999 on 20 Nov. 1990. Since then it has become an accepted and widely instrument disinfectant chemical active for the disinfection of endoscopes and metallic surgical reusable instruments. It is currently marketed internationally either as a ready-to-use 0.3 or 0.5% w/w buffered aqueous solution. It is predominantly used in totally enclosed washer-disinfector machines, of which several models are available.

OPA is marketed competitively with chemical sterilants based on glutaraldehyde or peracetic acid, which are similarly intended for the disinfection of endoscopes. Each chemical type of formulation has distinctive properties with respect to the effective spectrum of micro-organisms it will kill (or permanently inactivate) in normal process cycles, chemical hazard, corrosivity to metals and surgical plastics, chemical stability as packaged products, and most importantly economy of use.

Of these alternative chemical sterilants, peracetic acid, whilst being the most corrosive, toxic and expensive, has the better anti-microbial spectrum.

OPA, while odourless at low vapour concentration, is nevertheless quite toxic, has a very good anti-microbial spectrum but the serious limitation of poor sporicidal activity.

Glutaraldehyde has the operational problem of a strong, distinctive and irritant odour when used as a two part alkali activated solution. The more widely use formulation of glutaraldehyde, covered by U.S. Pat. No. 4,748,279, contains glutaraldehyde complexed together with a glycol and non-ionic surfactant. This emits less odour and has an improved biocidal spectrum. Like OPA it has a very good anti-microbial spectrum and is by far the most economical and flexile of the group. When employed in sealed processing equipment, the recommended method of use, each group of chemicals is free of operational hazard.

OPA, being only slightly soluble in water, is presently manufactured as a chemical disinfectant, comprising a simple aqueous solution marketed either as containing 0.3 or 0.5 percent w/w of active material. The solution is buffered to pH 7-8 wherein OPA is most effective as a biocide and remains chemically stable for some months at a temperature of 15-30 degree Celsius.

The general biocidal properties of the commercial product by Johnson & Johnson of CIDEX 0.5% OPA is well discussed in the paper by Alfa M J et al: *In hospital evaluation of orthophthaldehyde as a high level disinfectant for endoscopes*. J. Hospital Infection (1994) 26, 15-26.

In water OPA, like other dialdehydes, forms an equilibrium mixture of several hydrates, the properties of which are strongly influenced by pH. The chemistry of aqueous solutions of OPA is thoroughly described by Zhu P C, et al. *Solvent or Matrix mediated Molecular Switches in Lipophilic dialdehyde (OPA) and the Ampholytic 1,3-phthaladiol and OPA Disinfection Machanism*. Current Organic Chemistry, 2005, 1155-1166. The hydrates on the carbonyl group subsequently resolve to form an equilibrium mixture of OPA and 1,3-phthalandiol depending on concentration, temperature and pH.

This mechanism is illustrated as a biocidal limitation of OPA when presented as dilute 0.3 and 0.5% w/w aqueous solutions, biocidal action being of either a lipophilic or amphipilic nature dependent on the equilibrium mixture within a limited pH range.

An important feature of dilute (0.5%) aqueous OPA is its sensitivity to the presence of the types of surfactants commonly found in medical detergents. The existence of an equilibrium mixture of dilute (0.5%) aqueous OPA and 1,3-phthalandiol is seriously affected when mixed with most classes of surfactants due to uptake of molecular OPA (and its aqueous derivatives) into micelles. This restricts the availability and reactivity of OPA (and its derivatives) to the potentially reactive surface components of microbes, an important problem when dilute OPA is employed in mechanical washer-disinfectors where inadequate removal of pre-cleaning detergents before exposure of instruments to OPA is frequently encountered in practice.

The other serious operational disadvantages of packaged dilute OPA are both its sensitivity to storage conditions and its cost to the user as a ready-to-use product.

Recent research has clearly demonstrated that improved formulations of OPA can overcome these latter disadvantages whilst providing improved biocidal spectrum, a much needed requirement for the automatic cleaning and disinfection of endoscopes and metallic surgical instruments.

Overcoming the majority of the problems of using OPA as a chemical disinfectant was the basis of the recent International Patent WO 2008/116271 A to R K Whiteley et al. which described compositions including at least one mono or dialdehyde (including OPA) at least one glycol or polyol or derivative thereof, a nonionic first surfactant, a second surfactant having cloud point in the range 30-50° C., wherein the second surfactant is a quaternary compound.

It is well understood that an aldehyde may react with an alcohol to produce an acetal. In the case of a 1,2-diol or 1,3 diol, reaction with an aldehyde will produce a cyclic acetal which on the whole, tend to be more stable than acyclic acetals.

Since this is an equilibrium process, in a large molar excess of alcohol, production of the acetal will be favoured, whereas in the presence of a large molar excess of water, the equilibrium will favour the production of the free aldehyde (see FIG. 1). In the absence of acid, this equilibrium process will be suppressed.

In the case of a dialdehyde such as OPA, a more complex set of equilibria may be established under acid catalysed conditions, resulting in an equilibrium mixture of the free aldehyde, the monoacetal and diacetal derivatives. It is also possible for the mixture to contain hemiacetals.

The formation of acetals from aldehyde based disinfectant solutions has previously been described, and has been utilised as a means to control the odour of glutaraldehyde based disinfectants. For example, Australian Patent No. 562017 describes biocidal compositions in which glutaraldehyde is reacted with polyhydric alcohols such as polyethylene glycol, diethylene glycol or triethylene glycol to form a biocidal composition with reduced odour. From the test data presented in AU 562017, the biocidal activity of the acetal containing formulation was similar to that of glutaraldehyde itself. It should be noted however that the formulations described in AU 562017 had pH values below 7, and hence the products described presumably existed as an equilibrium mixture.

The use of acetals of OPA have also been described, albeit as a means to obtain aqueous solutions of free OPA, U.S. Pat. No. 5,872,153 for example, describes a method of producing an OPA-glutaraldehyde disinfecting compositions in which an OPA acetal is added to an aqueous solution of glutaraldehyde, and the mixture distilled under reduced pressure to remove the alcohol liberated from the acetal. Since the final biocidal mixture is a mixture of free OPA and glutaraldehyde, there is no data to suggest any biocidal efficacy attributable to the OPA acetals.

DESCRIPTION OF THE INVENTION

Figure 1:
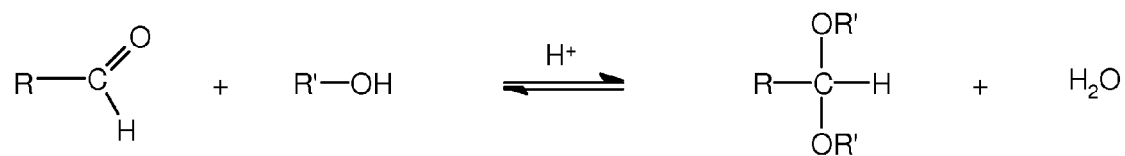
FIG. 1 shows the schematic representation of the reaction between and aldehyde and an alcohol to produce an acetal.

According to a first aspect, the invention provides for a high level disinfectant or sterilant based on a synergistic mixture of a dialdehyde and a non-equilibrium mixture of mono- and diacetal derivatives of the dialdehyde. In a second aspect, the invention provides the means of producing a synergistic blend of OPA and OPA mono- and diacetal derivatives that are particularly efficacious against mycobacterium such as *Mycobacterium Terrae*.

Disinfectant solutions based on OPA are commercially available for the high level disinfection and/or sterilisation of heat sensitive medical devices such as flexible endoscopes. In order to be classified as a high level disinfectant, the solution is required by most regulatory bodies such as the US Food and Drugs Administration (FDA) and the Australian Therapeutic Goods Agency (TGA) to achieve a minimum of a 6 log reduction against a panel of organisms including bacteria, mycobacterial spp, a range of viruses, fungi and both aerobic and anaerobic spore forming bacteria, including bacterial species such as *Pseudomonas aeruginosa, E. coli, Staphylococcus aureus* and a mycobacterium such as *M. terrae*. Testing of the disinfectant is performed as the active ingredients minimum effective concentration (MEC). The time required to achieve the required 6 log reduction is then used as the minimum recommended contact time between the disinfectant and the device to be disinfected.

The most challenging organisms for a high level disinfectant are normally the mycobacteria, since these organisms have a waxy outer coating that makes the bacteria less susceptible to chemical disinfectants.

One commercially available disinfectant, Cidex OPA (produced by Johnson and Johnson) has a MEC of 0.3% OPA, and a minimum high level disinfection time of 10 minutes at 20° C. for manual disinfection, and 5 minutes at 25° C. when used in an automatic endoscope reprocessor.

Given the fact that a particular endoscope may be required for use several times during a single day, and that high level disinfection of said scope is required before each use, there is a clear imperative that reliable disinfection be achieved in the shortest possible time. There is also a clear market advantage for any solution that can achieve the required disinfection at a lower temperature, as this avoids the need to heat and maintain the disinfectant at a set temperature.

It has been discovered by the inventors that an aqueous disinfectant solution comprising an aldehyde, a polyol and the corresponding mono and diacetal reaction products of the aldehyde and polyol show a marked increase in efficacy against mycobacteria when compared to a disinfectant solution in which the acetal species are absent.

In a preferred embodiment of the invention, the aldehyde is an aromatic aldehyde, and in a particularly preferred embodiment, the aldehyde is an aromatic dialdehyde.

Most preferred is when the aldehyde is o-phthalaldehyde (OPA). The aldehyde content of the final disinfectant solution will be between 0.2% w/v and 5% w/v.

The polyol may be selected from the non limiting list containing ethylene glycol, 1,2-propylene glycol, 1,3-propylene glycol, 1,2-butyl glycol, 1,3-butyl glycol, 1,4-butyl glycol, 1,2-cyclopropanediol, 1,2-cyclohexanediol. In a preferred embodiment, the polyol should be a 1,2-diol or a 1,3-diol, and in a highly preferred embodiment, the polyol should be a 1,2-diol. Most preferred is 1,2-propanediol (hereafter referred to as propylene glycol, or PG). The molar ratio of aldehyde to polyol within the final disinfectant solution is preferably between 2 and 20, and more preferably between 10 and 20.

Preferably the disinfectant solution will also contain surfactants. These may be non-ionic, anionic, cationic or zwitterionic. Preferably, the surfactants will be non-ionic, as disclosed in the applicants co-pending application WO 2008116271.

In a preferred embodiment, the aldehyde is dissolved into an excess of the polyol, along with a trace amount of acid, and the mixture warmed gently to allow the formation of a mixture comprising the aldehyde, the polyol, and acetals derived from the aldehyde and polyol. The mixture is then added to an aqueous solution containing buffer salts, surfactants and optionally other ingredients such as corrosion inhibitors, antifoaming agents, colourants etc.

The pH of the disinfectant solution will preferably be held to between 7.00 and 10.00, or more preferably between 7.00 and 8.00. The pH is controlled by one or more buffering agents selected from, but not limited to: phosphoric acid, monosodium phosphate, disodium phosphate, trisodium phosphate, boric acid, sodium tetraborate, citric acid, monosodium citrate, disodium citrate, trisodium citrate. A person skilled in the art will also recognise that other salts will be equally suited.

In a more preferred embodiment, the aldehyde is dissolved into the polyol, and the solution treated with an acid such as phosphoric acid, and then heated to between 30 and 50° C. The resultant solution, containing a mixture of acetal derivatives, along with a small quantity of free aldehyde is then added to a solution comprising water, free aldehyde, buffer salts and surfactants.

The solution may also contain other optional ingredients such as colourants, antifoaming agents, corrosion inhibitors and chelating agents. A secondary biocide may also be incorporated into the formulation. Non-limiting examples of secondary biocides includes phenol derivatives such as triclosan, o-phenyl phenol, etc, quaternary ammonium biocides such as benzalkonium chloride, polyhexamethylene biguanide and the like.

Example 1

Propylene glycol (46.0) was placed in a beaker and warmed to between 30° C. and 40° C., and OPA (5.75 g) added with stirring. The mixture was stirred at this temperature until all of the OPA dissolved. The solution was then allowed to cool to room temperature, and then stood overnight. Acid catalysis was provided by the trace levels of acetic acid present in the propylene glycol.

Meanwhile, a solution of disodium phosphate (11.34 g) and monosodium phosphate (0.96 g) in deionised water (918.77 g) was prepared. To this solution was added Neodol 91-6 (21.56 g) and Pluronic PE 6200 (7.19 g), and the mixture stirred until homogenous. The solution of OPA in propylene glycol was then added. Analysis of the resultant solution showed an OPA concentration of 0.307% w/v. An additional 3.35 g of OPA was then added, and the mixture stirred until dissolved. Analysis by titration showed an OPA concentration of 0.575% w/v. The pH of the final product was 7.80.

Example 2

To a mixture of Neodol 91-6 (21.56 g) and Pluronic PE 6200 (7.19 g) was added OPA (5.75 g). The mixture was stirred at room temperature until the OPA had fully dissolved (3 hours).

Meanwhile, a solution of disodium phosphate (11.34 g), monosodium phosphate (0.96 g) and propylene glycol (46.0 g) in deionised water (918.77 g) was prepared. To this solution was added the surfactant-OPA solution. The mixture was stirred until homogenous. Analysis of the resultant solution showed an OPA concentration of 0.575% w/v. The pH of the solution was 7.82.

Both samples of disinfectant were found to have the same concentration of OPA, when assayed by titration. However when assayed by GLC, a marked difference in OPA concentration was observed (see Table 1).

TABLE 1

Comparison of batch analyses

| | % OPA added (gravimetric) | Analysis by Titration | Analysis by GLC |
|---|---|---|---|
| Example 1 | 0.91 | 0.575 | 0.48 |
| Example 2 | 0.575 | 0.575 | 0.575 |

Since the titration is performed under acidic conditions (pH 3: see below for detailed description of method), whereas the GLC analysis is performed under essentially neutral conditions (the pH of the analytical samples was 7.8), it is likely therefore that Sample 1 contains an acid labile material.

Figure 3:
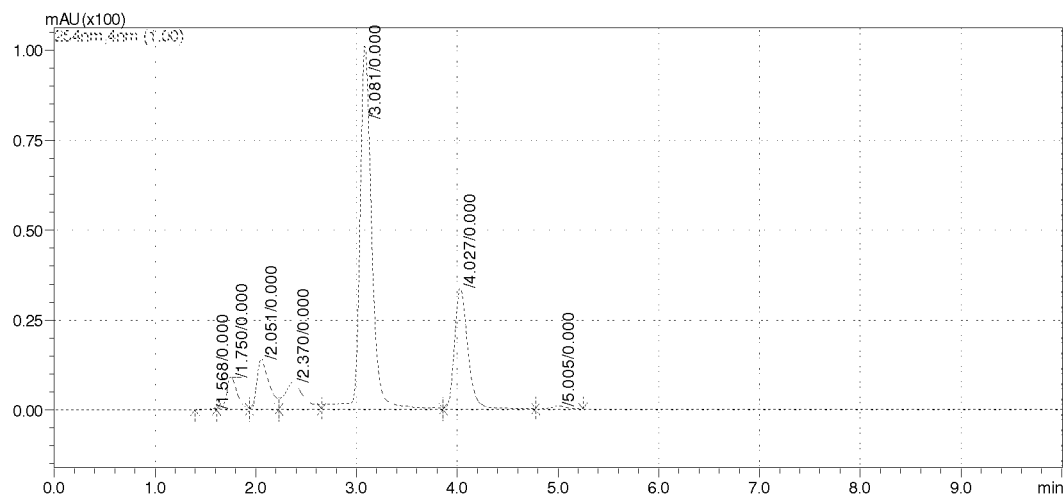
FIG. 3 is the HPLC trace obtained from example 1.
Figure 4:
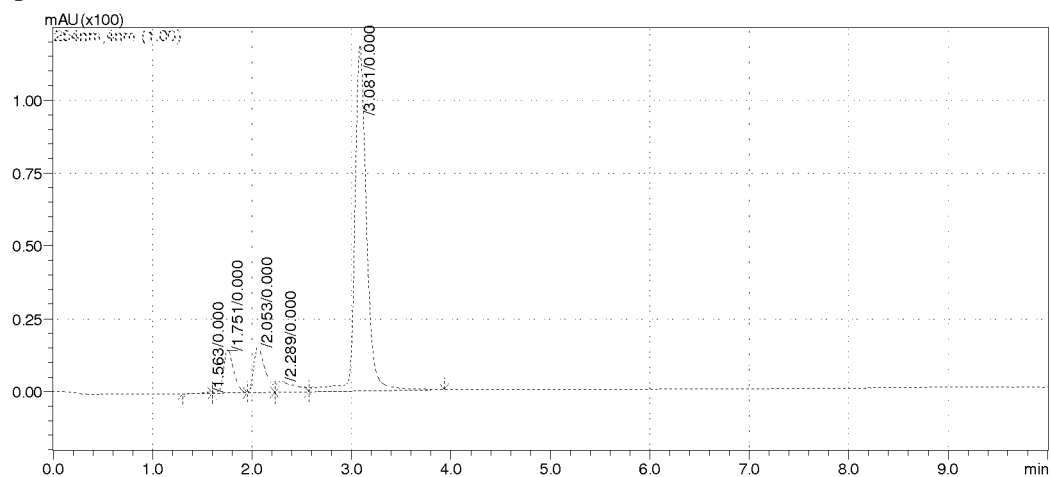
FIG. 4 is the HPLC trace obtained from example 2.
Figure 5:
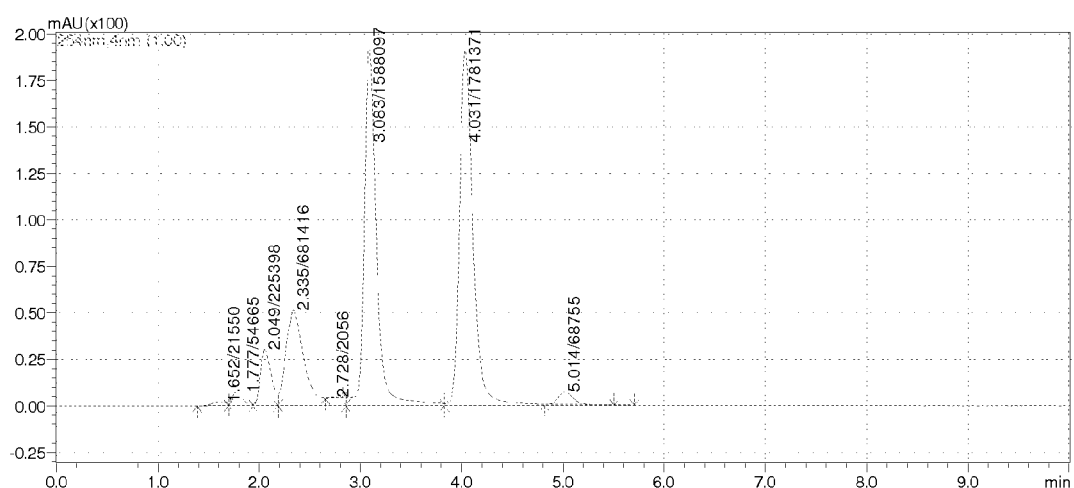
FIG. 5 is the HPLC trace obtained from example 3.

When subjected to qualitative analysis by HPLC, additional peaks were observed in example 1 which were absent in example 2 (see FIGS. 3 and 4).

Figure 2:
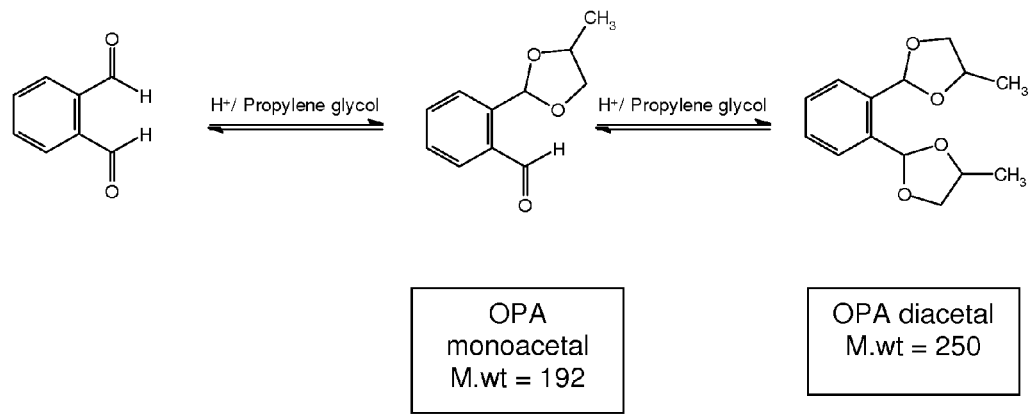
FIG. 2 illustrates the reaction between OPA and propylene glycol to produce a monoacetal and a diacetal.

LC-MS analysis indicated that the peak at retention time 4 minutes had a molecular weight of 192, and the peak at 5 minutes had a molecular weight of 250. These molecular weights are consistent with OPA monoacetal and OPA diacetal respectively (see FIG. 2).

The difference observed between the titration analysis and the GLC analysis in Sample 1 is likely therefore to be due to the presence of OPA monoacetal within the sample. Given that additional OPA is released when the sample is acidified, it is clear that the OPA and acetals exist in a non-equilibrium solution, by virtue of the solution pH being above 7.

On acidification (and therefore addition of acid catalysis), the concentrations of OPA and acetals shifts to the equilibrium position, which, in the presence of a large excess of water, lies to the side of free OPA and propylene glycol.

It is therefore likely that the difference between the expected gravimetric concentration and the titrated concentration is due to the diacetal. Without wishing to be bound by theory, it is most likely that the diacetal derivative is very insoluble in water, and therefore is likely to reside exclusively within the micelles formed by the surfactants within the disinfectant. The micelles would isolate the diacetal and prevent hydrolysis by aqueous acid.

Comparative Biocidal Performance

Both sample 1 and sample 2 were assessed for their biocidal performance against a panel of 4 micro-organisms, using the Option B tests described in the Australian Therapeutic Goods Agency's Therapeutic Goods Order No. 54 (TGO 54) performance standards for disinfectants. In the case of the Option B testing, two concentrations were assessed: a 1:1 dilution with water and a 1:3 dilution in water.

The samples were also tested against *Micobacterium Terrae*, using the AOAC testing methodology. In the testing against *M. Terrae*, the samples were diluted to give an OPA concentration of 0.3%.

TGO 54 Option B Testing (50% Dilution)

TABLE 2

Example 1: 50% dilution (nominal OPA concentration 0.29%)

| | Growth in recovery broths | | |
|---|---|---|---|
| Organism | Challenge 1 | Challenge 2 | Result |
| *Pseudomonas Aeruginosa* NCTC 6749 | ----- | ----- | Pass |
| *Escherichia Coli* NCTC 8186 | ----- | ----- | Pass |
| *Proteus Vulgarius* NCTC 4635 | ----- | ----- | Pass |
| *Staphylococcus Aureus* NCTC 4163 | ----- | ----- | Pass |

TABLE 3

Example 2 (nominal OPA concentration 0.29%)

| | Growth in recovery broths | | |
|---|---|---|---|
| Organism | Challenge 1 | Challenge 2 | Result |
| *Pseudomonas Aeruginosa* NCTC 6749 | ----- | ----- | Pass |
| *Escherichia Coli* NCTC 8186 | ----- | ----- | Pass |
| *Proteus Vulgarius* NCTC 4635 | ----- | ----- | Pass |
| *Staphylococcus Aureus* NCTC 4163 | ----- | ----- | Pass |

TABLE 4

Example 1 (nominal OPA concentration 0.15%)

| | Growth in recovery broths | | |
|---|---|---|---|
| Organism | Challenge 1 | Challenge 2 | Result |
| *Pseudomonas Aeruginosa* NCTC 6749 | ----- | +++++ | FAIL |
| *Escherichia Coli* NCTC 8186 | ----- | ----- | Pass |
| *Proteus Vulgarius* NCTC 4635 | ----- | ----- | Pass |
| *Staphylococcus Aureus* NCTC 4163 | ----- | ----- | Pass |

TABLE 5

Example 2 (nominal OPA concentration 0.15%)

| | Growth in recovery broths | | |
|---|---|---|---|
| Organism | Challenge 1 | Challenge 2 | Result |
| Pseudomonas Aeruginosa NCTC 6749 | - - - - - | - + + + + | FAIL |
| Escherichia Coli NCTC 8186 | - - - - - | - - - - - | Pass |
| Proteus Vulgarius NCTC 4635 | - - - - - | - - - - - | Pass |
| Staphylococcus Aureus NCTC 4163 | - - - - - | - - - - - | Pass |

TABLE 6

Test organism Mycobacterium terrae (20° C.: nominal OPA concentration 0.3%)

| Lot No. | Manufacturing method | 5 minute log reduction |
|---|---|---|
| Example 1 | Method 1 | >7 log |
| Example 1 | Method 1 | >7 log |
| Example 2 | Method 2 | <6 log |
| Example 2 | Method 2 | <6 log |

As may be seen in the above biocidal efficacy results, whilst disinfectant example 1 shows comparable performance with of example 2 in the Option B testing against a panel of 4 organisms (tables 2-5), there is a clear and distinct improvement in the biocidal activity of example 1 as compared to example 2 when tested against *M. Terrae* (table 6).

It is clear therefore that the presence of acetal derivatives in example 1 acts synergistically with free OPA against mycobacteria.

The quantity of acetal derivatives present in the OPA-propylene glycol premix of example 1 may be controlled in several ways.

Firstly, an increase in the temperature at which the premix is dissolved will increase the relative quantities of acetal derivatives within the final product.

Secondly, if the time between generating the OPA-propylene glycol premix, and its addition to the remaining ingredients is increased, then so will the quantity of acetal derivatives formed.

Finally, an increase in the acidity will favour formation of the acetal derivatives, and this is illustrated in example 3.

Example 3

Propylene glycol (46.0) was placed in a beaker and warmed to between 30° C. and 40° C., and 85% phosphoric acid (0.40 g) added. OPA (5.75 g) was then added with stirring. The mixture was stirred at this temperature until all of the OPA dissolved. The solution was then allowed to cool to room temperature, and then stood overnight.

Meanwhile, a solution of disodium phosphate (11.92 g) in deionised water (918.77 g) was prepared. To this solution was added Neodol 91-6 (21.56 g) and Pluronic PE 6200 (7.19 g), and the mixture stirred until homogenous. The solution of OPA in propylene glycol was then added. Analysis of the resultant solution showed an OPA concentration of 0.146% w/v. The pH of the final product was 7.80.

As may be seen in table 7, example 2 contained no detectable acetal derivatives. Deliberate acidification of the propylene glycol prior to addition of the OPA (example 3) led to an increase in the levels of both the mono and diacetal derivatives, along with a relative increase in the level of diacetal as compared to the monoacetal.

TABLE 7

| | HPLC Peak Areas | | | Peak area ratios | | |
|---|---|---|---|---|---|---|
| Sample | OPA | monoacetal | Diacetal | OPA/diacetal | OPA:monoacetal | Monoacetal/diacetal |
| Example 1 | 825270 | 308652 | 7536 | 2.7 | 109.5 | 41.0 |
| Example 2 | 857955 | Not detected | Not detected | — | — | — |
| Example 3 | 1588097 | 1781371 | 68755 | 0.9 | 23.1 | 25.9 |

The ratio of monoacetal to diacetal may be controlled by the initial ratio of OPA to propylene glycol. In Examples 1 and 3, the molar ratio of propylene glycol to OPA was 14.7. A reduction of the molar ratio will tend to favour the production of monoacetal over diacetal, and thus allow a degree of control over the final product composition.

Figure 6:
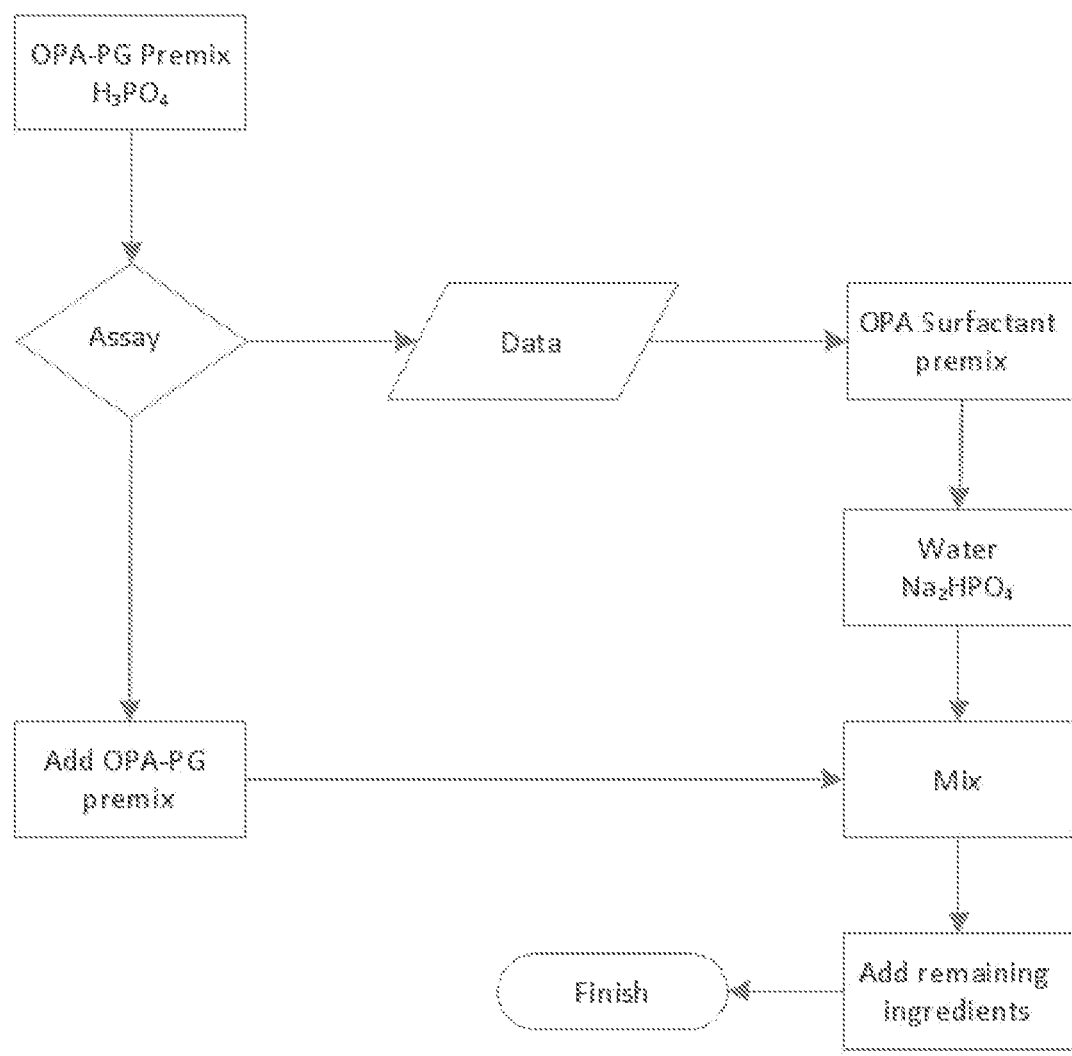
FIG. 6 is a schematic representation of a process to control the level of acetal derivatives in the final product.

The level of free OPA, OPA monoacetal and OPA diacetal in the final disinfectant solution may therefore be controlled, and the process flow is illustrated schematically in FIG. 6.

Step 1

Propylene glycol is initially acidified with 85% propylene glycol, and OPA is added. The mixture is warmed gently and stirred until all of the OPA has dissolved. The molar ratio of propylene glycol:OPA may be selected to produce the desired ratio of mono and diacetal in the final product. The resultant solution may be assayed by GLC to assess the quantity of OPA remaining unreacted in the solution.

Step 2

In a second mixing vessel, the surfactants are combined, and OPA added. The quantity of OPA to be added will be equal to the desired final OPA content minus the quantity of free OPA remaining in the propylene glycol-OPA solution. The surfactant/OPA mixture is stirred until all of the OPA has dissolved.

Step 3

The OPA-surfactant mixture from step 2 is added to a solution of disodium phosphate in water. The quantity of disodium phosphate is calculated so as to produce a pH of between 7.5 and 8.0 in the final disinfectant solution, allowing for the phosphoric acid added to the propylene glycol in step 1.

Step 4

The solution of OPA in propylene glycol from step 1 is added to the solution produced in step 3, and stirred until homogenous.

Step 5

Any other ingredients, such as colourants, antifoaming agents, corrosion inhibitors and chelating agents, along with any additional propylene glycol are added to the solution in step 4.

The final disinfectant solution is now ready for packing into bottles.

The acetal derivatives may also be isolated by solvent extraction, optionally followed by column chromatography, and added to a disinfectant solution containing no acetals (such as that described in example 2). The isolation procedure is illustrated in example 4.

Example 4

Propylene glycol (46.0) was placed in a beaker and warmed to between 30° C. and 40° C., and 85% phosphoric acid (0.40 g) added. OPA (5.75 g) was then added with stirring. The mixture was stirred at this temperature until all of the OPA dissolved. The solution was then allowed to cool to room temperature, and then stood overnight.

The resultant solution is then poured into a separating funnel, and a solution of sodium carbonate in water added (100 ml), along with 100 ml of dichloromethane. The mixture is shaken, and then allowed to stand. The lower organic layer is then removed, and the aqueous phase extracted a further 2 times with dichloromethane (50 ml).

The organic extracts are combined, washed with water (2×100 ml), followed by a brine wash. The organic phase is then dried over magnesium sulphate, and the solvent removed to yield a straw coloured mobile liquid. HPLC of this liquid shows it to contain predominantly the mono and diacetal derivatives of OPA, along with a small quantity of free OPA.

Chromatography on alumina, eluting with a mixture of hexane and ethyl acetate allows separation of the free OPA, the monoacetal derivative and the diacetal derivative.

Test Methods
OPA Assay by Titration

A solution of 10% hydroxylamine hydrochloride was taken, and its pH adjusted to 3.00 by the addition of 0.1M sodium hydroxide solution.

20 g of the 0.55% OPA solution is accurately weighed into a 150 ml beaker, and diluted to 100 ml with deionised water. The pH of the resultant solution is then adjusted to 3.00 by the addition of hydrochloric acid. To this solution is added 20 ml of a 10% hydroxylamine hydrochloride solution, whose pH has been adjusted to 3.00 with sodium hydroxide solution.

The mixture is stirred for at least 5 minutes, and then titrated with 0.1M sodium hydroxide solution to a pH of 3.00.

The concentration of OPA is then given by $$\% OPA = [v \ast N \ast 67.05 \ast 100/(W \times 1000)]$$

Where:
v=ml of NaOH titrate
N=molarity of NaOH
W=weight of sample in grams.
67.05=equivalent weight of OPA OPA by GLC 5 ml of a standard OPA solution with a concentration of 0.5% w/v is pipette into a vial, along with 5 ml of a 1% solution of benzyl alcohol in water. Benzyl alcohol is added as an internal standard). An aliquot of the resultant solution is taken and placed in a 12×32 mm auto sampler vial, and analysed by GLC using the following conditions:

| Column: | Restek Stabilwax 30 m × 0.32 |
|---|---|
| Carrier gas | Helium |
| Column flow rate | 2.17 ml/min |
| Injection port temperature | 200° C. |
| Split ratio | 46 |
| FID temperature | 250° C. |
| Oven temperatures | |
| Initial temperature | 120° C. |
| Initial hold time | 0 min |
| Temperature ramp | 5° C./minute |
| Final temperature | 220° C. |
| Final hold time | 8 minutes |

The above is repeated using 5 ml of the OPA solution to be assayed. The concentration of the unknown sample is given by $$\% OPA = (WR_{st} \times AR_{unk} \times C_{st})/(AR_{st})$$

Where,
$AR_{st}$=Peak Area ratio of OPA to Internal Standard in working standard
$AR_{unk}$=Peak Area ratio of OPA to Internal Standard in test sample
$WR_{st}$=ratio of concentrations of OPA and internal standard in working standard
$C_{st}$=concentration of internal standard solution

HPLC

HPLC analysis was performed using a 150×2 mm C18 reverse phase column, eluting at 0.2 ml/min with a mixture of 60% Acetonitrile and 40% aqueous solution of 10 mMol phosphate buffer (pH6.0). Detection was performed using a UV-visible detector tuned to 254 nm.

LC-MS was performed using the same chromatographic conditions, with the exception being the buffer was changed to ammonium acetate. Ionisation was performed using an ESI probe.

Qualitative GLC

Qualitative GLC analysis was performed as described for the OPA analysis, with the exception being an additional heating phase was added to the oven program.

The invention claimed is:

1. A disinfectant solution comprising:
    a. an aldehyde;
    b. a polyol;
    c. one or more acetal derivatives formed by reaction of said aldehyde with said polyol;
    d. one or more surfactants selected from the general classes anionic, cationic, or non-ionic;
    e. one or more pH buffering agents selected from the group consisting of monosodium phosphate, disodium phosphate, trisodium phosphate, sodium tetraborate, sodium bicarbonate, sodium citrate, phosphoric acid, boric acid and citric acid;
    wherein the disinfectant solution is made from a process wherein the aldehyde reacts with the polyol prior to the remaining ingredients being added, and the extent of reaction between said aldehyde and said polyol is controlled by adjusting the molar ratio of polyol to aldehyde to between 2 and 20.

2. The disinfectant solution of claim 1 wherein the aldehyde is a dialdehyde.

3. The disinfectant solution of claim 2 wherein the dialdehyde is an aromatic dialdehyde.

4. The disinfectant solution of claim 3 wherein the dialdehyde is o-phthalaldehyde.

5. The disinfectant solution of claim 1 wherein the polyol is a diol.

6. The disinfectant solution of claim 5 wherein the diol is a 1,2-diol.

7. The disinfectant solution of claim 5 wherein the diol is a 1,3-diol.

8. The disinfectant solution of claim 1 wherein the polyol is selected from the group consisting of ethylene glycol, propylene glycol, butyl glycol and cyclohexylenediol.

9. The disinfectant solution of claim 1 wherein the polyol is selected from the group consisting of propylene glycol, butyl glycol and cyclohexylenediol.

10. A disinfectant solution according claim 5 wherein the acetal is produced by an acid catalyzed reaction between said aldehyde and said diol.

11. A disinfectant solution according to claim 5 wherein both a monoacetal and a diacetal is produced by an acid catalyzed reaction between a dialdehyde and said diol.

12. A disinfectant solution according to claim 11 wherein the pH of the solution is held between pH 7.0 and pH 10.0.

13. A disinfectant solution according to claim 11 wherein the ratios of free aldehyde, and acetal derivatives are held in a non-equilibrium ratio.

14. A disinfectant solution according to claim 1 wherein an aldehyde assay obtained by titration at pH 3 is greater than an aldehyde assay obtained by gas-liquid chromatography under neutral conditions.

15. A disinfectant solution according to claim 12 that demonstrates a higher log reduction of mycobacteria than a solution containing no acetal derivatives.

16. A disinfectant solution according to claim 12 that demonstrates a higher log reduction of mycobacteria than a solution in which an aldehyde assay obtained by titration at pH 3 is equal to an aldehyde assay obtained by gas-liquid chromatography under neutral conditions.

17. A disinfectant solution according to claim 1 comprising one or more optional ingredients selected from the group consisting of coloring agents, antifoaming agents, corrosion inhibiting agents, secondary biocidal agents and chelating agents.

18. A process of producing a disinfectant solution, said disinfectant solution comprising:
    a. an aldehyde;
    b. a polyol;
    c. one or more acetal derivatives formed by reaction of said aldehyde with said polyol;
    d. one or more surfactants selected from the general classes anionic, cationic, or non-ionic; and
    e. one or more pH buffering agents selected from the group consisting of monosodium phosphate, disodium phosphate, trisodium phosphate, sodium tetraborate, sodium bicarbonate, sodium citrate, phosphoric acid, boric acid and citric acid;
    wherein the aldehyde reacts with the polyol prior to the remaining ingredients being added.

19. A process of producing the disinfectant solution according to claim 18 wherein an acid is added to a mixture of said aldehyde and said polyol.

20. A process according to claim 18 wherein the extent of reaction between said aldehyde and said polyol is controlled by adjusting the molar ratio of polyol to aldehyde to between 2 and 20.

21. A process according to claim 20 wherein the molar ratio of polyol to aldehyde is adjusted to between 2 and 5.

22. A process of producing a disinfectant solution according to claim 18 wherein an acidic solution of said polyol and said aldehyde is added to an aqueous solution of said aldehyde.

23. A method of disinfecting and/or sterilizing a heat sensitive medical device, said method comprising treating said medical device with a disinfectant solution, said disinfectant solution comprising:
    a. an aldehyde;
    b. a polyol;
    c. one or more acetal derivatives formed by reaction of said aldehyde with said polyol;
    d. one or more surfactants selected from the general classes anionic, cationic, or non-ionic; and
    e. one or more pH buffering agents selected from the group consisting of monosodium phosphate, disodium phosphate, trisodium phosphate, sodium tetraborate, sodium bicarbonate, sodium citrate, phosphoric acid, boric acid and citric acid;
    the aldehyde reacting with the polyol prior to the remaining ingredients being added, and the extent of reaction between said aldehyde and said polyol is controlled by adjusting the molar ratio of polyol to aldehyde to between 2 and 20.

\* \* \* \* \*